United States Patent [19]

Krass

[11] 4,227,916

[45] Oct. 14, 1980

[54] CONTROL OF WEEDS WITH 1-(3-METHYL-5-ISOTHIAZOLYL)-3-ALKOXYL-3-METHYLUREAS

[75] Inventor: Dennis K. Krass, Canal Fulton, Ohio

[73] Assignee: PPG Industries, Inc., Pittsburgh, Pa.

[21] Appl. No.: 71,170

[22] Filed: Aug. 30, 1979

Related U.S. Application Data

[62] Division of Ser. No. 848,174, Nov. 4, 1977.

[51] Int. Cl.$^2$ ............................................. A01N 9/12
[52] U.S. Cl. ....................................................... 71/90
[58] Field of Search ............................................ 71/90

[56] References Cited

U.S. PATENT DOCUMENTS

| | | | |
|---|---|---|---|
| 3,454,591 | 7/1969 | Schulz | 260/306.8 |
| 3,922,160 | 11/1975 | Buttmore | 71/90 |
| 4,057,415 | 11/1977 | Ramsey | 71/90 |

*Primary Examiner*—Donald G. Daus
*Assistant Examiner*—Lisa Jones
*Attorney, Agent, or Firm*—Robert J. Grassi

[57] ABSTRACT

Disclosed are 3-methyl-5-isothiazolyl-3-alkoxyureas, such as 1-(3-methyl-5-isothiazolyl)-3-methoxy-3-methylurea, and the method of controlling broadleaf and grassy weeds, such as *Echinochloa crusgalli* (L.) Beauv. (barnyardgrass), with these ureas.

6 Claims, No Drawings

CONTROL OF WEEDS WITH 1-(3-METHYL-5-ISOTHIAZOLYL)-3-ALKOXYL-3-METHYLUREAS

This is a division of application Ser. No. 848,174, filed Nov. 4, 1977.

BACKGROUND OF THE INVENTION

1. Field of the Invention

The invention pertains to isothiazolyl ureas, particularly 1-(3-methyl-5-isothiazolyl)-3-alkoxy-3-methylureas, such as 1-(3-methyl-5-isothiazolyl)-3-methoxy-3-methylurea, and the method of controlling weeds with these ureas.

2. Description of the Prior Art

*The Herbicide Handbook of the Weed Science Society of America*, 3rd. Edition (1974), obtainable from the Weed Science Society of America, 425 Illinois Building, 113 N. Neal Street, Champaign, Illinois 61820, shows the following commercial ureas used to control weeds: 3-(4-bromo-3-chlorophenyl)-1-methoxy-3-methylurea, page 93; m-(3,3-dimethylureido)phenyl-tert-butyl carbamate, page 220; 3-[p-(p-chlorophenoxy)-phenyl]-1,1-dimethylurea, page 98; 3-(p-chlorophenyl)-1,1-dimethylurea, monotrichloroacetate, page 225; 3-(3,4-dichlorophenyl)-1,1-dimethylurea, page 172; 3-(3,4-dichlorophenyl)-1-methoxy-1-methylurea, page 221; 1,1-dimethyl-3-(α,α,α-trifluoro-m-tolyl)urea, page 194; and 3-(hexahydro-4,7-methanoindan-5-yl)-1,1-dimethylurea, page 280. Also disclosed is the cyclic urea 1-(2-methylcyclohexyl)-3-phenylurea, page 356.

Other ureas giving herbicidal activity are disclosed in U.S. Pat. No. 3,454,591 (1-(3-methyl-5-isothiazolyl)-3,3-dimethylurea), U.S. Pat. No. 3,622,593 (1-(5-isothiazolyl)-3,3-dimethylurea), French Pat. No. 2,132,691 (1-(3-methyl-4-ethoxycarbonyl-5-isothiazolyl)-3-methylurea), Netherlands application No. 6,605,902 (1-(3-methyl-5-isothiazolyl)-3-methylurea), U.S. Pat. No. 3,922,160 (1-(3-methyl-4-cyano-5-isothiazolyl)-3,3-dimethylurea), German Offenlegungsschrift 2,434,922 (1-(3-methyl-4-cyano-5-isothiazolyl)-3-methoxy-3-methylurea), and German Offenlegungsschrift 2,408,234 (1-(3-methyl-4-acetyl-5-isothiazolyl)-3-methoxy-3-methylurea).

U.S. Pat. No. 3,563,985 describes a method for preparing ureas, carbamates, and thiocarbamates having a 3- or 5-isothiazolyl ring attached to one of the nitrogen atoms thereof.

SUMMARY OF THE INVENTION

The invention concerns agriculturally useful compounds of 1-(3-methyl-5-isothiazolyl)-3-methoxy-3-methylurea, 1-(3-methyl-5-isothiazolyl)-3-ethoxy-3-methylurea, 1-(3-methyl-5-isothiazolyl)-1-methyl-3-methoxy-3-methylurea, and 1-(3-methyl-5-isothiazolyl)-1-methyl-3-ethoxy-3-methylurea. These compounds are useful for controlling broadleaf weeds and annual grasses, and 1-(3-methyl-5-isothiazolyl)-3-methoxy-3-methylurea is particularly effective against the weeds described herein.

DETAILED DESCRIPTION OF THE INVENTION

The isothiazolyl ureas contemplated herein are those of 1-(3-methyl-5-isothiazolyl)-3-methoxy-3-methylurea, 1-(3-methyl-5-isothiazolyl)-3-ethoxy-3-methylurea, 1-(3-methyl-5-isothiazolyl)-1-methyl-3-methoxy-3-methylurea, and 1-(3-methyl-5-isothiazolyl)-1-methyl-3-ethoxy-3-methylurea, and are used as herbicides for the control of annual grasses and broadleaf weeds, particularly for the weeds described herein.

The compounds 1-(3-methyl-5-isothiazolyl)-3-methoxy-3-methylurea and 1-(3-methyl-5-isothiazolyl)-1-methyl-3-methoxy-3-methylurea are highly preferred, and 1-(3-methyl-5-isothiazolyl)-3-methoxy-3-methylurea is the most preferred.

SYNTHESIS

In general the, compounds may be prepared by reacting 5-amino-3-methylisothiazole or 3-methyl-5-N-methyl aminoisothiazole with a phenyl (or a substituted phenyl) chloroformate to form the corresponding carbamate, then reacting the carbamate with the appropriate alkyl-alkoxy-amine, so as to form the 1-(3-methyl-5-isothiazolyl)-3-alkoxy-3-methylurea, or the 1-(3-methyl-5-isothiazolyl)-1-methyl-3-alkoxy-3-methylurea, where the alkoxy is methoxy or ethoxy.

Another general method of synthesis for the compounds of 1-(3-methyl-5-isothiazolyl)-3-methoxy-3-methylurea or 1-(3-methyl-5-isothiazolyl)-3-ethoxy-3-methylurea consists of reacting the 3-methyl-5-aminoisothiazolyl with phosgene to form the 3-methyl-5-isothiazolylisocyanate (the isocyanate at the 5 position of the isothiazole ring) and then reacting this with the appropriate alkyl-alkoxy-amine so as to form the respective 1-(3-methyl-5-isothiazolyl)-3-methoxy-3-methylurea or 1-(3-methyl-5-isothiazolyl)-3-ethoxy-3-methylurea.

The following examples illustrate the method of synthesizing these compounds.

EXAMPLE I

Synthesis of 1-(3-Methyl-5-isothiazolyl)-3-methoxy-3-methylurea

A 250 milliliter, 3-neck, round bottom flask was charged with 6.84 grams (0.06 mole) of 5-amino-3-methylisothiazole and 100 milliliters of dry pryridine. The flask was fitted with a thermometer and adapter, a 25 milliliter pressure-equalizing funnel, drying tube, and a stopper. The solution was cooled to 3 degrees (3° C.) Centigrade and then 9.36 grams (0.06 mole) of phenylchloroformate was added dropwise, at such a rate that the reaction temperature was maintained at/or below 6 degrees (6° C.) Centigrade. The phenylchloroformate was added over a 25 minute period, resulting in the formation of a white solid. The solution was stirred for 1½ hours at 3 degrees (3° C.) Centigrade and then slowly poured into 600 milliliters of ice water. The solid was filtered and dried affording 10.57 grams of a crude product containing O-phenyl-N-(3-methyl-5-isothiazolyl)carbamate. Recrystallization of the crude product from ethyl acetate/benzene mixture (volume ratio of 30 to 70) yielded 7.0 grams of purified O-phenyl-N-(3-methyl-5-isothiazolyl)carbamate having a melting point of 186 to 188.5 degrees (186° to 188.5° C.) Centigrade. The infrared spectrum (mull) had the following maximum frequencies: $\nu = 3085$, 2920, 1720, 1580, and 1390 centimeters$^{-1}$ (cm$^{-1}$). The nuclear magnetic resonance (NMR) spectrum in dimethylsulfoxide-d$_6$ (DMSO-d$_6$) is 2.62$\delta$ (3H, singlet, —CH$_3$); 7.07$\delta$ (1H, singlet, ring 4-H); 7.45$\delta$ to 7.83$\delta$ (5H, multiplet, phenyl H's), and 11.53$\delta$ (1H, singlet, NH).

A 100 milliliter flask was charged with a solution of 50 milliliters of tetrahydrofuran (THF) containing 4.68 grams (0.02 mole) of the above mentioned purified O-phenyl-N-(3-methyl-5-isothiazolyl)carbamate, and 1.22 grams (0.02 mole) of O,N-dimethylhydroxylamine was added. The solution was stirred for 50 hours at ambient temperature. The amine was prepared by stirring the commercial amine-hydrochloride salt in 50 percent (50%) potassium hydroxide solution, distilling off the amine, and collecting that fraction having a boiling point of 42 to 43 degrees (42° to 43° C.) Centigrade at atmospheric pressure.

Thin layer chromatography showed no reaction had occurred; consequently, an additional 1.0 gram of O,N-dimethylhydroxylamine was added and the reaction mixture was refluxed for 3 days. This reaction mixture, when examined by thin layer chromatography, contained O-phenyl-N-(3-methyl-5-isothiazolyl)carbamate and a new product. The solvent was removed by vacuum from the reaction mixture leaving a viscous, pale-yellow oil which was triturated with 50 milliliters of ethyl ether to form a solid powder. The solid powder, after being washed well with ethyl ether to remove the phenol, was placed in a reaction flask and dissolved in 25 milliliters of tetrahydrofuran (THF), 3.0 grams of O,N-dimethylhydroxylamine was added, and the solution was refluxed overnight.

After the solvent was removed from the refluxed solution, the residue was triturated with ethyl ether, and filtered to yield 2.34 grams of a white powdered material containing about 80 percent (80%) of 1-(3-methyl-5-isothiazolyl)-3-methoxy-3-methylurea and the remaining 20 percent (20%) being unreacted starting material of O-phenyl-N-(3-methyl-5-isothiazolyl)carbamate, which is herbicidally ineffective. The white powdered material was recrystallized from a mixture of ethanol and ethylacetate (volume ratio 1 to 1 and quantity 25 milliliters) to yield a white powder which was approximately 90 percent (90%) 1-(3-methyl-5-isothiazolyl)-3-methoxy-3-methylurea, and had a melting point of 164 to 167 degrees (164° to 167° C.) Centigrade. Its infrared spectra $v_{mull}{}^{max}$ 3150, 1660, and 1540 centimeters$^{-1}$ (cm$^{-1}$). Its nuclear magnetic resonance (NMR) spectrum in dimethylsulfoxide-d$_6$ (DMSO-d$_6$) was 2.58$\delta$ (3H, singlet, —CH$_3$); 3.43$\delta$ (3H, singlet, —CH$_3$); 4.04$\delta$ (3H, singlet, —CH$_3$); 7.13$\delta$ (1H, singlet, ring 4-H), and 11.28$\delta$ (1H, singlet, NH). Its mass spectrum showed a molecular ion at m/e (mass over electron charge) 201.

The following example illustrates a preferred method of synthesis of 1-(3-methyl-5-isothiazolyl)-3-methoxy-3-methylurea.

EXAMPLE II

A 500 milliliter, 3-necked flask fitted with a low temperature thermometer and adapter, a 60 milliliter pressure-equalizing addition funnel, and a drying tube (Dnerite) was charged with 22.8 grams (0.2 mole) of 5-amino-3-methylisothiazole and 350 milliliters of pyridine. After the flask was cooled in an ice bath, 31.2 grams (0.2 mole) of phenyl chloroformate was added to the addition funnel, and when the solution in the flask reached 3 degrees (3° C.) Centigrade, the addition of phenyl chloroformate was begun, and addition was continued at a rate which maintained the reaction temperature at/or below 8 degrees (8° C.) Centigrade, (addition was complete after 1 hour). The funnel was removed, the flask stoppered, and the reaction mixture stirred for 20 hours at ambient temperature.

The reaction mixture was poured into 1200 milliliters of ice water (2 liter beaker) and vigorously stirred for 15 minutes and then filtered. The solid was pressed dry, returned to a 2 liter beaker, and stirred with 1500 milliliters of distilled water for half an hour, filtered, washed well with water, and dried at 70 degrees (70° C.) Centigrade in a vacuum oven. The total crude yield was 43.4 grams (93 percent), and the melting point was 180 to 186 degrees (180° to 186° C.) Centigrade. The dried solid was recrystallized from methanol (volume 100 milliliters) to yield a total of 26.4 grams of white needles of O-phenyl-N-(3-methyl-5-isothiazolyl)carbamate having a melting point of 185 to 188 degrees (185° to 188° C.) Centigrade, (purified yield 57 percent). The infrared spectra of white needles of O-phenyl-N-(3-methyl-5-isothiazolyl)carbamate was: $v_{mull}{}^{max}$ 3200-2600, 1720, 1580, 1495, and 1230 centimeters$^{-1}$ (cm$^{-1}$). Its nuclear magnetic resonance (NMR) spectrum in UNISOL-d ® (Norell Co.) (1 to 1 volume ratio of deuterochloroform and dimethylsulfoxide-d$_6$) was 2.40$\delta$ (singlet, 3H), 6.71$\delta$ (singlet, 1H), 7.0-7.73$\delta$ (multiplet, 5H), and 11.53$\delta$ (singlet, 1H). Its mass spectrum showed a molecular ion at m/e 234.

A 200 milliliter flask was filled with 100 milliliters of dry tetrahydrofuran (THF) and 18.72 grams (0.08 mole) of the purified O-penyl-N-(3-methyl-5-isothiazolyl)carbamate mentioned above. The flask was warmed on a steam bath until the solid dissolved and was then cooled to 25 degrees (25° C.) Centigrade. Methoxymethylamine (obtained from its hydrochloride salt by distilling from a 50 weight percent potassium hydroxide solution, boiling point 42 to 43 degrees Centigrade) was added in one portion, 4.88 grams (0.08 mole), to the solution. A condenser and drying tube were attached to the flask, and the solution was stirred and refluxed for 3 days. An additional 4.88 grams (0.08 mole to replace that volatized during refluxing) was added and refluxing was continued for an additional 15 hours, at which time thin layer chromatography indicated complete conversion of the O-phenyl-N-(3-methyl-5-isothiazolyl)carbamate to 1-(3-methyl-5-isothiazolyl)-3-methoxy-3-methylurea. The solvent was stripped, leaving a viscous pale-yellow oil (phenol and urea) which was diluted with 50 milliliters of ethyl ether and chilled in an ice bath. The resultant solid was filtered, washed well with ethyl ether, stirred with 75 milliliters of ethyl ether, and refiltered to yield 14.35 grams of a white powder of substantially pure 1-(3-methyl-5-isothiazolyl)-3-methoxy-3-methylurea, having a melting point of 159 to 166 degrees (159° to 166° C.) Centigrade. Recrystallization of 1 gram of the white powder gave 0.56 gram of white platelets with a melting point of 164 to 167 degrees (164° to 167° C.) Centigrade, an infrared spectra of $v_{mull}{}^{max}$ 3130, 2990, 1660, and 1540 centimeters$^{-1}$ (cm$^{-1}$); a nuclear magnetic resonance (NMR) spectrum in UNISOL-d ® (1 to 1 volume ratio of deuterochloroform and dimethylsulfoxide-d$_6$) of 2.33$\delta$ (singlet, 3H), 3.18$\delta$ (singlet, 3H), 3.72$\delta$ (singlet, 3H), 6.76$\delta$ (singlet, 1H), and 10.67$\delta$ (singlet, 1H); and a mass spectrum with a molecular ion at m/e/ 201.

In the syntheses shown in Examples I and II above, the recrystallization step of the O-phenyl-N-(3-methyl-5-isothiazolyl)carbamate can be avoided by keeping the reaction temperature below 10 degrees (10° C.) Centigrade and washing the crude product with water until no pyridine odor is present. The requirement of adding methoxymethylamine to replace that lost by volatilization can be avoided by using a sealed tube.

APPLICATION

The compounds contemplated herein may be used as herbicides, particularly against annual grasses and broadleaf weeds described herein. The most preferred compound, 1-(3-methyl-5-isothiazolyl)-3-methoxy-3-methylurea, is particularly effective at low application rates against the weeds described herein, as shown by the following tests:

PROCEDURE

Postemergence And Preemergence Testing

Screened topsoil, which had been limed to a pH of 6.5, mixed with sand and vermiculite (12:3:3 vol/vol), and had been fertilized with 12-12-12 farm grade fertilizer at a rate of about one hundred (100) pounds per acre of total nitrogen, was placed in plastic two and three-quarter (2.75) inch square pots to a depth of about two and five-tenths (2.5) inches. Single weed species were grown per pot, by placing the seeds of a single weed species on top of the soil in the pot, and covering them with one-quarter (0.25) inch of soil. The number of seeds of a weed species per pot varied from about eight (8) to forty (40) depending upon the particular weed species grown in the pots.

For postemergence testing, the weed species were planted according to a growth cycle to insure that at the time of postemergence testing of the compounds, that the weed plant emerging had at least one true leaf, e.g., cocklebur was planted prior to grasses, such as barnyardgrass. The pots after being seeded were watered and placed in the laboratory growth room where the weeds were grown under artificial light from GRO-LUX ® fluorescent lights at a temperature of about 23 to 33 degrees (23° to 33° C.) Centigrade and a relative humidity of 50 to 80 percent (50 to 80%), until the emerging plants had several true leaves.

For preemergence testing, the seeds of the weed species were planted one day before spraying. The pots after being seeded were watered and placed in the laboratory growth room prior to spraying with the test compounds.

The test compound was dissolved in a standard solvent mixture of acetone, methanol, dimethylformamide (90:8:2 vol/vol) and diluted to the appropriate concentration, and was applied postemergence to the leaves at a predetermined rate, e.g., 482 milligrams of the test compound per 4.63 square feet, which is equivalent to 10 pounds of active ingredient per surface acre (10 lbs. ai/acre, by means of a herbicidal sprayer. For lower rates of application, the solution was diluted with distilled water to obtain the predetermined application rate. The sprayer was equipped with a Tee-Jet 8001 spray nozzle tip and the sprayer operated in the range of 35 to 40 pounds per square inch pressure with compressed air. The sprayer was set to deliver fifty (50) gallons of solution per surface acre.

The potted plants, which had at least one true leaf, were placed on a tray, and the tray was placed on a conveyor belt which passed through the sprayer at about nine-tenths (0.9) foot per second. The tray tripped a microswitch which activated a solenoid valve to release the spray solution containing the test compound.

Immediately after the spray treatment, the sprayed pots of weeds were transferred to the above mentioned growth room and held there for visual observations of the weeds. Daily observations were made for interim changes in the weeds and a final observation was made thirteen (13) days and twenty-two (22) days after the postemergence spray treatment. This final observation included abnormal physiological changes such as stem bending, petiole curvature, epinasty, hyponasty, retardation, stimulation, root development, necrosis, and retarded growth regulant characteristics.

These observations were reported as Injury Ratings based on a relative scale of zero (0) to ten (10); zero (0) meaning no observed injury or control, and ten (10) meaning severe injury resulting in complete control, all plants were killed. The abnormal physiological ratings were reported as necrosis (Ne), chlorosis (Cl), retardation (R), regrowth occurring (Z), and no visual abnormal responses, zero (0).

EXAMPLE III

When solid powder from Example I containing 80 percent (80%) of 1-(3-methyl-5-isothiazolyl)-3-methoxy-3-methylurea was applied post-emergence at 10 pounds of active ingredient per acre (11 kilograms/hectare), according to the procedure described above for postemergence testing, the following results, shown in Table I, were obtained.

Column 1 of Table I gives the weed species, both its scientific and common name, and Column 2 gives the control rating at 13 and 22 days and the physiological response obtained.

TABLE I

POSTEMERGENCE CONTROL AT 10 POUNDS OF ACTIVE INGREDIENT/ACRE OF 1-(3-METHYL-5-ISOTHIAZOLYL)-3-METHOXY-3-METHYLUREA

| Weed Species | Control Rating 13 days | 22 days | Abnormal Response |
|---|---|---|---|
| *Xanthium pensylvanicum* (L.) common cocklebur | 9 | 10 | Necrosis |
| *Datura stramonium* (L.) jimsonweed | 10 | 10 | Necrosis |
| *Brassica kaber* (D.C.) wild mustard | 10 | 10 | Necrosis |
| *Gossypium hirsutum* (L.) (Coker variety) cotton | 9 | 9 | Necrosis; Regrowth Occurring |
| *Sesbania spp.* coffeeweed | 9 | 9 | Necrosis |
| *Abutilon theophrasti* (L.) velvetleaf | 10 | 10 | Necrosis |
| *Ipomoea spp.* morningglory | 10 | 10 | Necrosis |
| *Echinochloa crusgalli* (L.) Beauv. barnyardgrass | 10 | 10 | Necrosis |
| *Avena fatua* wild oats | 8 | 10 | Necrosis |
| *Cypress esculentus* (L.) yellow nutsedge | 0 | 0 | 0 - No Response |
| *Sorghum halepense* (L.) johnsongrass | | 3 | Necrosis; Retardation |
| *Setaria glauca* (L.) yellow foxtail | 9 | 10 | Necrosis |

EXAMPLE IV

When solid powder from Example 1 containing 80 percent (80%) of 1-(3-methyl-5-isothiazolyl)-3-methoxy-3-methylurea was applied post-emergence as in Example III but at five (5) pounds per acre (5.5 kilograms/hectare), the following results given in Table II were obtained at the end of a 14 day observation period.

Column 1 of Table II gives the weed species, both its scientific and common name, and Column 2 gives the control rating at 14 days, and the physiological response obtained.

TABLE II

POSTEMERGENCE CONTROL AT 5 POUNDS OF ACTIVE INGREDIENT/ACRE OF 1-(3-METHYL-5-ISOTHIAZOLYL)-3-METHOXY-3-METHYLUREA

| Weed Species | Control Rating 14 Days | Abnormal Response |
|---|---|---|
| *Xanthium pensylvanicum* (L.) common cocklebur | 10 | Necrosis |
| *Datura stramonium* (L.) jimsonweed | 10 | Necrosis |
| *Brassica kaber* (D.C.) wild mustard | 10 | Necrosis |
| *Gossypium hirsutum* (L.) (Coker variety) cotton | 10 | Necrosis |
| *Sesbania* spp. coffeeweed | 9 | Necrosis |
| *Abutilon theophrasti* (L.) velvetleaf | 10 | Necrosis |
| *Ipomoea* spp. morningglory | 10 | Necrosis |
| *Echinochloa crusgalli* (L.) Beauv. barnyardgrass | 10 | Necrosis |
| *Avena fatua* wild oats | 10 | Necrosis |
| *Cypress esculentus* (L.) yellow nutsedge | 0 | 0 - No Response |
| *Sorghum halepense* (L.) johnsongrass | 5 | Necrosis |
| *Setaria glauca* (L.) yellow foxtail | 8 | Necrosis |

EXAMPLE V

When the solid powder from Example I containing 90 percent (90%) of 1-(3-methyl-5-isothiazolyl)-3-methoxy-3-methylurea was applied postemergence as in Example III, but at 2 pounds per acre (2.2 kilograms/hectare), the following results shown in Table III were obtained at the end of a 14 day observation period.

Column 1 of Table III gives the weed species, both its scientific and common name, and Column 2 gives the control rating at 14 days and the physiological response obtained.

TABLE III

POSTEMERGENCE CONTROL AT 2 POUNDS OF ACTIVE INGREDIENT/ACRE OF 1-(3-METHYL-5-ISOTHIAZOLYL)-3-METHOXY-3-METHYLUREA

| Weed Species | Control Rating 14 Days | Abnormal Response |
|---|---|---|
| *Xanthium pensylvanicum* (L.) common cocklebur | 8 | Necrosis |
| *Datura stramonium* (L.) jimsonweed | 10 | Necrosis |
| *Brassica kaber* (D.C.) wild mustard | 10 | Necrosis |
| *Gossypium hirsutum* (L.) (Coker variety) cotton | 7 | Necrosis; Regrowth Occurring |
| *Sesbania* spp. coffeeweed | 7 | Necrosis |
| *Abutilon theophrasti* (L.) velvetleaf | 10 | Necrosis |
| *Ipomoea* spp. morningglory | 10 | Necrosis |
| *Echinochloa crusgalli* (L.) Beauv. barnyardgrass | 10 | Necrosis |
| *Avena fatua* wild oats | 10 | Necrosis |
| *Cypress esculentus* (L.) yellow nutsedge | 0 | 0 - No Response |
| *Sorghum halepense* (L.) johnsongrass | 2 | Necrosis |
| *Setaria glauca* (L.) yellow foxtail | 3 | Necrosis |

EXAMPLE VI

When the solid powder from Example I containing 90 percent (90%) of 1-(3-methyl-5-isothiazolyl)-3-methoxy-3-methylurea was applied preemergence at 10 pounds of active ingredient per acre (11 kilograms/hectare) according to the procedure for preemergence testing described above, the following results shown in Table IV were obtained.

Column 1 of Table IV gives the weed species, both its scientific and common name, and Column 2 gives the control rating at 13 and 22 days, respectively, and the physiological response obtained.

TABLE IV

PREEMERGENCE CONTROL AT 10 POUNDS OF ACTIVE INGREDIENT/ACRE OF 1-(3-METHYL-5-ISOTHIAZOLYL)-3-METHOXY-3-METHYLUREA

| Weed Species | Control Rating 13 Days | Control Rating 22 Days | Abnormal Response |
|---|---|---|---|
| *Xanthium pensylvanicum* (L.) common cocklebur | 3 | 7 | Retardation; Necrosis |
| *Datura stramonium* (L.) jimsonweed | 5 | 8 | Retardation, Chlorosis, and Necrosis |
| *Brassica kaber* (D.C.) wild mustard | 10 | 10 | Chlorosis; Necrosis |
| *Setaria glauca* (L.) yellow foxtail | 8 | 8 | Retardation; Necrosis |
| *Sesbania* spp. coffeeweed | 8 | 10 | Retardation; Necrosis |
| *Abutilon theophrasti* (L.) velvetleaf | 9 | 10 | Retardation; Necrosis |
| *Cypress esculentus* (L.) yellow nutsedge | 0 | 0 | 0 - No Response |
| *Sorghum halepense* (L.) johnsongrass | 5 | 5 | Retardation; Necrosis |
| *Digitaria sanguinalis* (L.) crabgrass | 9 | 10 | Retardation; Necrosis |
| *Ipomoea* spp. morningglory | 4 | 4 | Retardation; Necrosis |
| *Echinochloa crusgalli* (L.) Beauv. barnyardgrass | 2 | 7 | Necrosis; Retardation |

TABLE IV-continued
PREEMERGENCE CONTROL AT 10 POUNDS OF ACTIVE INGREDIENT/ACRE OF 1-(3-METHYL-5-ISOTHIAZOLYL)-3-METHOXY-3-METHYLUREA

| Weed Species | Control Rating | | Abnormal Response |
|---|---|---|---|
| | 13 Days | 22 Days | |
| *Avena fatua* wild oats | 2 | 3 | Necrosis |

EXAMPLE VII

When solid powder from Example I containing 80 percent (80%) 1-(3-methyl-5-isothiazolyl)-3-methoxy-3-methylurea was applied preemergence as in Example VI but at 5 pounds per acre (5.5 kilograms/hectare), the following results, shown in Table V, were obtained after a 14 day observation period.

Column 1 of Table V gives the weed species, both its scientific and common name, and Column 2 gives the control rating at 14 days, and the physiological response obtained.

TABLE V
PREEMERGENCE CONTROL AT 5 POUNDS OF ACTIVE INGREDIENT/ACRE OF 1-(3-METHYL-5-ISOTHIAZOLYL)-3-METHOXY-3-METHYLUREA

| Weed Species | Control Rating 14 Days | Abnormal Response |
|---|---|---|
| *Xanthium pensylvanicum* (L.) common cocklebur | 3 | Retardation; Necrosis |
| *Datura stramonium* (L.) jimsonweed | 5 | Retardation, Chlorosis, and Necrosis |
| *Brassica kaber* (D.C.) wild mustard | 9 | Chlorosis; Necrosis |
| *Setaria glauca* (L.) yellow foxtail | 8 | Necrosis |
| *Sesbania* spp. coffeeweed | 8 | Retardation; Necrosis |
| *Abutilon theophrasti* (L.) velvetleaf | 9 | Retardation; Necrosis |
| *Cypress esculentus* (L.) yellow nutsedge | 3 | Retardation |
| *Sorghum halepense* (L.) johnsongrass | 4 | Retardation; Necrosis |
| *Digitaria sanguinalis* (L.) crabgrass | 10 | Necrosis |
| *Ipomoea* spp. morningglory | 6 | Retardation; Chlorosis |
| *Echinochloa crusgalli* (L.) Beauv. barnyardgrass | 6 | Necrosis |
| *Avena fatua* wild oats | 3 | Retardation; Necrosis |

EXAMPLE VIII

When solid powder from Example I containing 80 percent (80%) of 1-(3-methyl-5-isothiazolyl)-3-methoxy-3-methylurea was applied preemergence as in Example VI at 2 pounds per acre (2.2 kilograms/hectare), the following results shown in Table VI were obtained after a 14 day observation period.

Column 1 of Table VI gives the weed species, both its scientific and common name, and Column 2 gives the control rating at 14 days and the physiological response obtained.

TABLE VI
PREEMERGENCE CONTROL AT 2 POUNDS OF ACTIVE INGREDIENT/ACRE OF 1-(3-METHYL-5-ISOTHIAZOLYL)-3-METHOXY-3-METHYLUREA

| Weed Species | Control Rating 14 Days | Abnormal Response |
|---|---|---|
| *Xanthium pensylvanicum* (L.) common cocklebur | 0 | 0 - No Response |
| *Datura stramonium* (L.) jimsonweed | 2 | Chlorosis |
| *Brassica kaber* (D.C.) wild mustard | 8 | Chlorosis; Retardation |
| *Setaria glauca* (L.) yellow foxtail | 1 | Necrosis; Chlorosis |
| *Sesbania* spp. coffeeweed | 6 | Necrosis; Chlorosis |
| *Abutilon theophrasti* (L.) velvetleaf | 3 | Retardation; Chlorosis |
| *Cypress esculentus* (L.) yellow nutsedge | 1 | Retardation |
| *Sorghum halepense* (L.) johnsongrass | 1 | Necrosis |
| *Digitaria sanguinalis* (L.) crabgrass | 7 | Retardation; Chlorosis |
| *Ipomoea* spp. morningglory | 3 | Chlorosis |
| *Echinochloa crusgalli* (L.) Beauv. barnyardgrass | 1 | Chlorosis |
| *Avena fatua* wild oats | 1 | Chlorosis |

The herbicidal activity against weeds by the compounds described herein, and in particular broadleaf weeds, are illustrated by these last results. Although the herbicidally effective amount shown was for 10 pounds per acre (11 kilograms/hectare), such a dosage can be varied from 0.25 to 200 pounds per acre (0.27 to 220 kilograms/hectare), depending upon the species, growth stage, and the weather, but generally 0.25 to 50 pounds per acre will suffice, and under optimum conditions 0.25 to 10 pounds per acre is preferred.

Use of Formulations

Although the plants may be contacted with 1-(3-methyl-5-isothiazolyl)-3-methoxy-3-methylurea itself or with the other compounds contemplated therein, as directly synthesized or mixtures of the compounds described herein, or as granules, it is preferable to use other suitable agricultural formulations which contain other ingredients which enhance application of the compound or compounds. These agricultural formulations will generally comprise from 5 to 95 percent by weight of the ureas mentioned herein singularly or as a mixture of the compounds of the general formula. The mixture may include a trace of each of the other compounds mentioned herein or a substantial amount. The other ingredients of these formulations will be from 1 to 95 percent by weight of an agricultural diluent, or from 1 to 20 percent by weight of a surface active agent or other ingredients required to produce wettable powders, dusts, solutions, emulsifiable concentrates, granules, and the like.

Granules will contain from 5 percent to 25 percent active ingredient extended upon a granular base. When the toxicant compounds are solids, they may be dissolved in one or more solvents and then sprayed upon the absorptive carriers, such as attapulgite clay, synthetic fine silica, and synthetic calcium and sodium alumino-silicates. In some cases the solvent or solvents may later be evaporated off. Granules produced by extrusion or tumbling will contain like amounts of active ingredients.

Dusts are mixtures of the active compound with finely divided solids such as talc, attapulgite clay, kieselguhr, and other organic and inorganic solids which act as diluents and carriers for the compound. The finely divided solids have an average particle size of less than 50 microns. A typical dust formulation will contain from 1.0 to 10.0 parts by weight of one of the ureas mentioned herein or in mixture with the other compounds mentioned herein and from 99.0 to 90.0 parts by weight of talc.

Wettable powders for preemergent or postemergent application are finely divided solid particles, which disperse readily in water or other liquids. The wettable powder is applied to the soil, seed, or plant as a dry dust or as a water or other liquid emulsion.

Typical wettable powder carriers are Fuller's earth, Kaolin clays, silicas, and highly absorbent, readily wettable, inorganic diluents. Wettable powders normally contain about 5 to 80 weight percent of the active ingredient, depending on the absorbency of the carrier, and usually contain a small amount of a wetting, dispersing, or emulsifying agent to facilitate dispersion.

Other postemergent formulations are emulsifiable concentrates. These are homogeneous liquid or paste compositions which are dispersible in water or other liquids. They may consist entirely of one or more of the compounds mentioned herein and a liquid or solid emulsifying agent, or they may also contain a liquid solvent, such as xylene, heavy aromatic naphthas, or other nonvolatile organic solvents. These emulsifiable concentrates are dispersed in a liquid carrier, e.g., water, and generally are applied as a spray to the areas or plant to be treated. The weight percent of the urea compounds mentioned herein in these concentrates varies with the manner of application, but generally is from 0.5 to 95 percent.

Representative wetting, dispersing, and emulsifying agents for the agricultural formulations are alkyl and alkylaryl sulfonates and sulfates, and their alkali salts, polyethylene oxides, sulfoxided oils, fatty acid esters of polyhydric alcohols, and other surface-active agents, e.g., TWEEN 20®, a commercial surfactant. If used, the surfactant would vary from 0.25 to 15 weight percent of the composition.

Other formulations for herbicidal applications include simple solutions of the compound in solvents in which it is completely soluble at the desired concentration, e.g., acetone or other organic solvents, aerial spray formulations comprising relatively coarse particles coated with the urea compounds mentioned herein, and pressurized spray formulations, such as aerosols, which use low boiling dispersant solvents such as Freon. All of these formulations may be used to apply the active compound to the area to be treated.

These formulations may also include other agriculturally useful materials such as pesticides and herbicides which are non-toxic to the desired vegetation, but which are effective against other weeds, insects, microorganisms, and nematodes, so that one application will serve to rid the area of several undesirable species. For example, the ureas mentioned herein, such as 1-(3-methyl-5-isothiazolyl)-3-methoxy-3-methylurea, may be used with non-basic materials in formulations which contain other herbicides so as to increase the useful herbicidal spectrum of the thiazole, reduce the number of applications required by farmers and others who require use of these compounds to assist the healthful growth of crops.

These other materials can comprise from 5 percent (5%) to about 95 percent (95%) of the active ingredients in the herbicidal compositions. Use of combinations of these other herbicides and/or defoliants, dessicants, etc. with the compounds of the present invention provide herbicial compositions which are more effective in controlling weeds and often provide results unattainable with separate compositions of the individual herbicides. The herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, alachlor 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC and the like; thiocarbamate and dithiocarbamate herbicides such as CDEC, methan sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)-piperidine, and the like; chlorinated aliphatic acid herbicides such as TCA, dalapon, 2,3-dichloropopionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichobenil, DPA, dipheamid, dipropalin, trifluralin, solan, dicryl, merphos, DMPA, DSMA, MSMS, potassium azide, acrolein, benefin, bensulide, AMS, bromacil, 2-(3,4-dichlorophenyl)-4-methyl-1,2,4-oxadiazolidine-3,5-dione, bromozynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Effective Amounts to Apply

Normally, the effective amount of the compound to apply will vary with the environmental and climatic conditions.

When one or more of the compounds are applied in the form of a suitable agricultural composition, the application rate of such formulation is such that the amount of a compound, as active ingredient itself or in combination with other ingredients as mentioned herein, is an amount which is effective to control the weeds. As used herein and in the claims, the phrase "in an amount effective to control the weed", means that amount required to retard its normal growth by any of the physiological responses shown herein, such as by retardation, necrosis, chlorosis, etc., which hamper the growth of the weed so as to prevent it from competing with other desirable crops upon the land. Normally, the amount to apply varies from 0.25 pounds to 200 pounds per acre, but preferably, when the compound is 1-(3-methyl-5-isothiazolyl)-3-methoxy-3-methylurea, the amount would be from about 0.25 pounds per acre to 10 pounds per acre.

As used herein and in the claims, the phase "contacting the weed with a compound", refers to any method of contacting the weed, such as by applying the spray postemergent to the foliage of the weed, as well as, to the ground, or it could be by incorporating it into the ground for postemergence application. However, the preferred method of contacting the weed is by postemergent spraying.

The compound 1-(3-methyl-5-isothiazolyl)-3-methoxy-3-methylurea is preferably used postemergence against grassy weeds and broadleaf weeds at rates below 20 pounds per acre, particularly against weeds of the genus Xanthium, Datura, Brassica, Setaria, Sesbania, Abutilon, Gossypium, Ipomoea, Echinochloa, and Avena, preferably against the weed species *Xanthium pensylvanicum* (L.) (common cocklebur), *Datura stramonium* (L.) (jimsonweed), *Brassica kaber* (D.C.) (wild mustard), Sesbania spp. (coffeeweed), *Abutilon theophrasti* (L.) (velvetleaf), Ipomoea spp. (morningglory), *Echinochloa crusgalli* (L.) Beauv. (barnyardgrass), *Avena fatua* (wild oats), and *Setaria glauca* (L.) (yellow foxtail).

The compound 1-(3-methyl-5-isothiazolyl)-3-methoxy-3-methylurea is particularly useful at postemergence rates below 10 pounds per acre to control weed species of *Xanthium pensylvanicum* (L.) (common cocklebur), *Brassica kaber* (D.C.) (wild mustard), *Abutilon theophrasti* (L.) (velvetleaf), Ipomoea spp. (morningglory), *Echinochloa crusgalli* (L.) Beauv. (barnyardgrass), *Eleusine indica* (L.) (goosegrass), *Ipomoea muricata* (purple moon flower), *Amaranthus retroflexus* (L.) (redroot pigweed), *Cossia obtusifolia* (L.) (sicklepod), *Sida spinosa* (prickly sida), *Digitaria sanguinalis* (L.) (crabgrass), *Anoda cristata* (L.) (spurred anoda), and *Avena fatua* (wild oats).

The compound 1-(3-methyl-5-isothiazolyl)-3-methyloxy-3-methylurea is also particularly useful for preemergence control at rates below 10 pounds per acre of the weed species *Brassica kaber* (D.C.) (wild mustard), and *Digitaria sanguinalis* (L.) (crabgrass).

The compound 1-(3-methyl-5-isothiazolyl)-3-methoxy-3-methylurea is particularly effective for herbicidal use in crops of corn, sorghum, and peas at rates of below 1.0 pound per acre to control weeds of cocklebur, purple moon flower, sicklepod, prickly sida, or spurred anoda.

While the invention has been described with reference to specific details of certain illustrative embodiments, it is not intended that it shall be limited thereby except insofar as such details appear in the accompanying claims.

I claim:

1. A method of controlling broadleaf and grassy weeds which comprises contacting the weed with a compound in an amount effective to control the weed, said compound being a urea selected from the group consisting of:
1-(3-methyl-5-isothiazolyl)-3-methoxy-3-methylurea,
1-(3-methyl-5-isothiazolyl)-3-ethoxy-3-methylurea,
1-(3-methyl-5-isothiazolyl)-1-methyl-3-methoxy-3-methylurea, 1-(3-methyl-5-isothiazolyl)-1-methyl-3-ethoxy-3-methylurea or mixtures thereof.

2. The method of claim 1, wherein the weed is of a genus selected from the group consisting of Xanthium, Datura, Brassica, Setaria, Sesbania, Abutilon, Gossypium, Ipomoea, Echinochloa, and Avena.

3. The method of claim 1, wherein the weed is a species selected from the group consisting of *Xanthium pensylvanicum* (L.) (common cocklebur), *Datura stramonium* (L.) (jimsonweed), *Brassica kaber* (D.C.) (wild mustard), Sesbania spp. (coffeeweed), *Abutilon theophrasti* (L.) (velvetleaf), Ipomoea spp. (morningglory), *Echinochloa crusgalli* (L.) Beauv. (barnyardgrass), *Avena fatua* (wild oats), *Setaria glauca* (L.) (yellow foxtail), *Eleusine indica* (L.) (goosegrass), *Ipomoea muricata* (purple moon flower), *Amaranthus retroflexus* (L.) (redroot pigweed), *Cossia obtusifolia* (L.) (sicklepod), *Sida spinosa* (prickly sida), *Digitaria sanguinalis* (L.) (crabgrass), and *Anoda cristata* (L.) (spurred anoda).

4. The method of claim 1, wherein the compound is 1-(3-methyl-5-isothiazolyl)-3-methoxy-3-methylurea.

5. The method of claim 2, wherein the compound is 1-(3-methyl-5-isothiazolyl)-3-methoxy-3-methylurea.

6. The method of claim 3, wherein the compound is 1-(3-methyl-5-isothiazolyl)-3-methoxy-3-methylurea.

* * * * *